United States Patent [19]
Schroeppel

[11] Patent Number: 5,759,202
[45] Date of Patent: Jun. 2, 1998

[54] ENDOCARDIAL LEAD WITH LATERAL ACTIVE FIXATION

[75] Inventor: Edward A. Schroeppel, Lake Jackson, Tex.

[73] Assignee: Sulzer Intermedics Inc., Angleton, Tex.

[21] Appl. No.: 848,524

[22] Filed: Apr. 28, 1997

[51] Int. Cl.$^6$ ........................................ A61N 1/05
[52] U.S. Cl. ............................ 607/126; 600/375
[58] Field of Search ............................. 607/122, 123, 607/126, 127, 128, 130; 600/373–375, 377, 381

[56] References Cited

U.S. PATENT DOCUMENTS

| | | | |
|---|---|---|---|
| 3,902,501 | 9/1975 | Citron et al. | |
| 3,939,843 | 2/1976 | Smyth | |
| 3,943,936 | 3/1976 | Rasor et al. | |
| 4,233,992 | 11/1980 | Bisping | |
| 4,378,023 | 3/1983 | Trabucco | |
| 4,481,953 | 11/1984 | Gold et al. | 128/642 |
| 4,567,901 | 2/1986 | Harris | |
| 4,721,118 | 1/1988 | Harris | |
| 4,858,623 | 8/1989 | Bradshaw et al. | |
| 5,115,818 | 5/1992 | Holleman et al. | |
| 5,179,962 | 1/1993 | Dutcher et al. | |
| 5,257,634 | 11/1993 | Kroll | 607/122 |
| 5,314,462 | 5/1994 | Heil et al. | 607/128 |
| 5,385,579 | 1/1995 | Helland | 607/130 |
| 5,433,742 | 7/1995 | Willis | 607/122 |
| 5,476,500 | 12/1995 | Fain et al. | 607/126 |
| 5,571,162 | 11/1996 | Lin | 607/122 |
| 5,571,164 | 11/1996 | Ekwall et al. | 607/122 |
| 5,601,614 | 2/1997 | Ekwall | 607/25 |
| 5,676,694 | 10/1997 | Boser et al. | 607/122 |

FOREIGN PATENT DOCUMENTS

| | | | |
|---|---|---|---|
| 0 004 967A2 | 4/1979 | European Pat. Off. | A61N 1/04 |
| 3529578 A1 | 2/1987 | Germany | A61N 1/05 |

OTHER PUBLICATIONS

Kevin Morgan, et al., *A New Single Pass DDD Lead*, all pages, 8 May 1997.

Peter P. Karpawich, Septal Pacing: A New Approach to Improve Paced Left Ventricular Function; European Journal of Cardiac Pacing & Electrophysiology, vol. 6, No. 1, p. 143, Jun. 1996.

R. McVenes, What Tools Do We Need For Multi Site Stimulation?; European Journal of Cardiac Pacing & Electrophysiology, vol. 6, No. 1, p. 145, Jun. 1996.

Primary Examiner—Jeffrey R. Jastrzab
Attorney, Agent, or Firm—John R. Merkling

[57] ABSTRACT

A lead assembly adapted for transvenous implantation into a human heart is provided. The lead assembly includes a connector for electrical connection to a cardiac stimulator. An elongated sheath assembly projects from the connector. The sheath assembly includes an inner elastic insulating sheath that includes a coextensive lumen for receipt of a stylet. An outer elastic insulating sheath is disposed around the inner sheath, thereby defining an elongated annular space. The outer sheath has an aperture that defines a gripping region. A biasing wire is disposed in the annular space. The biasing wire is connected to the connector proximally and is approximately coterminous at its distal end with the outer sheath. The biasing wire has a plurality of coils exposed by the aperture in the gripping region. By first stretching and then relaxing the lead assembly, the coils of the biasing wire pinch small portions of the myocardium to laterally fix the lead assembly at a given location in the heart.

17 Claims, 5 Drawing Sheets

ENDOCARDIAL LEAD WITH LATERAL ACTIVE FIXATION

BACKGROUND OF THE INVENTION

1. Field of the Invention

This invention relates generally to cardiac stimulation leads. More particularly, this invention relates to endocardial stimulation leads that utilize active fixation.

2. Description of the Related Art

Cardiologists and cardiovascular surgeons are often confronted with cardiac arrhythmia patients who present arrhythmia symptoms that may be difficult to diagnose and treat. The difficulty presented by some of these patients stems from the fact that in some cases a patient's ability to pace normally may be adversely impacted by an electrical irregularity in only a very small region of the myocardium, or in several spatially separate regions. Consequently, the ability to accurately place endocardial stimulation electrodes provides the clinician with the opportunity for improved diagnosis and treatment of patients presenting various types of cardiac arrhythmia. Placement of a diagnostic lead proximate a suspected trouble spot in the myocardium may enable the practitioner to quickly zero in on the malfunctioning tissue and plot a treatment strategy. If pacing/defibrillation is indicated, it may then be desirable to accurately position and fix a lead electrode in a particular endocardial location. Placement of the electrode close to the malfunctioning tissue reduces the electrical thresholds necessary to achieve the required electrical stimulation. For example, it may be medically indicated to attach a defibrillation lead to a particular location on the interventricular septum, instead of relying on an electrode deposited in the ventricular apex.

In many instances it is desirable to attach more than one electrode at different points within the myocardium. The proposed use of chaos techniques to prevent or terminate tachyarrhythmias may require pacing at specific locations that have been determined by mapping studies. In such circumstances electrodes will have to be fixed at each location. Other patients may present arrhythmia symptoms which suggest simultaneous electrode positioning in both the ostium of the coronary sinus as well as one of the tributaries of the great cardiac vein.

Many solutions have been developed for fixing lead tip electrodes to a particular location within the myocardium. Some examples of these designs include lead tips with projecting tines or rabbit ears, cork screw electrodes, or side hook electrodes. While rabbit ear arrangements and cork screw tips may be suitable for fixing the tip of a lead to a particular location, those designs do not lend themselves to lateral fixation of more proximal portions of the lead since those designs focus primarily on fixing the tip of a lead. Furthermore, in any context where a hook attachment mechanism is utilized, care must be taken that the hooks are retractable or protectively coated during implantation and removal. In addition, such hooked lead tips may be impractical for thin-walled areas of the heart, such as the right atrium, or in areas where the myocardium has been thinned by disease or injury.

The conventional solution to fixing more than one electrode at different positions within the myocardium is to implant more than one lead. Where ventricular stimulation is involved, this option, by necessity, introduces more obstructions to the normal operation of the tricuspid valve as well as creates surgical complexities in the event that one or both of the leads have to be removed.

The present invention is directed to overcoming or reducing one or more of the foregoing disadvantages.

SUMMARY OF THE INVENTION

In accordance with one aspect of the present invention, a cardiac lead assembly is provided. The lead assembly includes a connector for attachment to a cardiac stimulator and a sheath assembly coupled to the connector. The sheath assembly includes a first elastic insulating sheath that has a lumen defined thereby. A first biasing wire is disposed around the first sheath that has a first plurality of coils and a distal end. A second elastic insulating sheath is disposed over and coupled to the first sheath and has an aperture that exposes at least two of the first plurality of coils. The at least two of the plurality of coils are operable to engage a portion of myocardial tissue therebetween when the lead assembly is moved from the expanded position to the retracted position.

In accordance with another aspect of the present invention, a cardiac lead assembly that has an expanded position and a retracted position is provided. The lead assembly includes a connector for attachment to a cardiac stimulator and a sheath assembly coupled to the connector. The sheath assembly includes a first elastic insulating sheath that has a lumen defined thereby. A first biasing wire is disposed around the first sheath. The first biasing wire has a first plurality of coils and a distal end. A second elastic insulating sheath is disposed over and coupled to the first sheath and has a first aperture that exposes at least two of the first plurality of coils. The at least two of said plurality of coils are operable to engage a portion of myocardial tissue therebetween when the lead is moved from the expanded position to the retracted position. A second biasing wire is disposed around the second sheath. The second wire has a second plurality of coils. An annular member is coupled to the second sheath and has a central opening of a first diameter disposed in the lumen. A third elastic insulating sheath is disposed over and coupled to the second sheath and has a second aperture that exposes at least two of the second plurality of coils. The at least two of the second plurality of coils are operable to engage a portion of myocardial tissue therebetween when a stylet having a diameter larger than the first diameter is inserted into the lumen and engages the annular member and the lead assembly is moved from the expanded position to the retracted position.

In accordance with still another aspect of the present invention, a cardiac stimulation system is provided. The cardiac stimulation system includes a cardiac stimulator and a cardiac lead assembly coupled to the cardiac stimulator. The lead assembly includes a first elastic insulating sheath and a biasing wire disposed around the first sheath. The biasing wire has a plurality of coils and a distal end. A second elastic insulating sheath is disposed over the first sheath and has an aperture that exposes at least two of the coils. The at least two coils are operable to engage a portion of myocardial tissue therebetween when the lead is moved from an expanded position to a retracted position.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
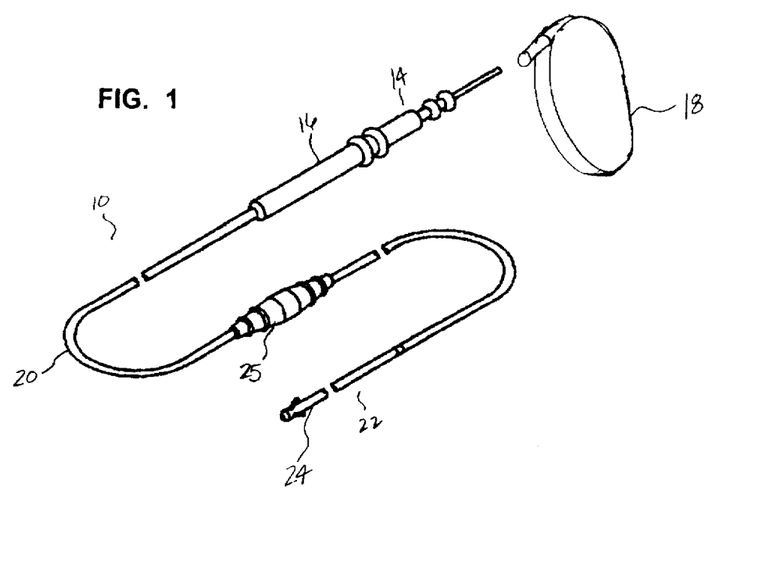
FIG. 1 is a pictorial view of an exemplary lead assembly in accordance with the present invention.
Figures 2, 3:
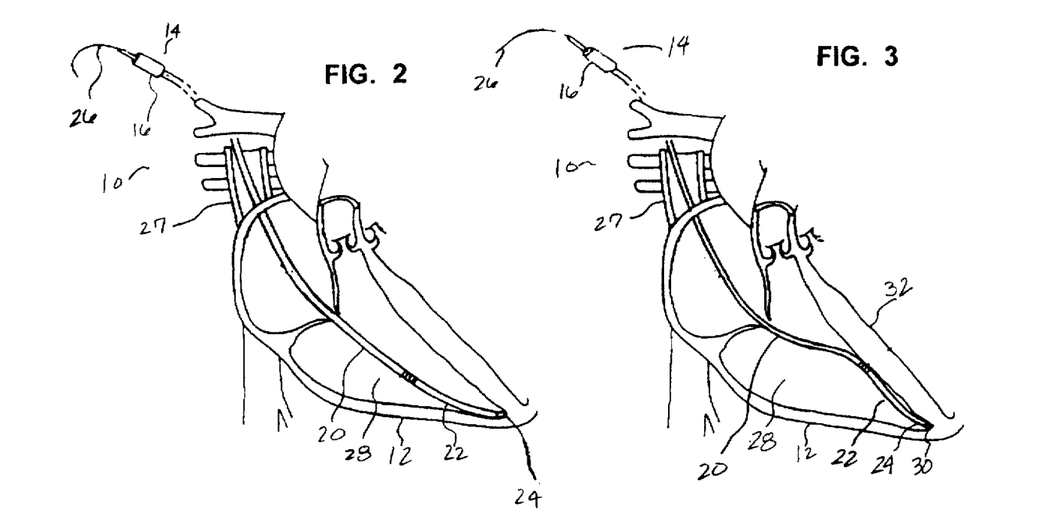
FIG. 2 is a partial cut away of a human heart showing the initial implantation stage for the lead assembly of FIG. 1.
FIG. 3 is a partial cut away of a human heart showing a subsequent implantation stage for the lead assembly of FIG. 1.

Turning now to the drawings, and in particular to FIGS. 1 and 2, there is shown an exemplary lead assembly 10 which is adapted for transvenous implantation into a human heart 12. Reference numerals are generally reused in the figures where identical elements appear in more than one figure. The lead assembly 10 includes a proximal end 14 that has a connector 16 for electrical connection to a cardiac stimulator 18. An elongated sheath assembly 20 extends distally from the connector 16. The distal end 22 of the sheath assembly 20 terminates in a tip 24. The lead assembly 10 also includes a suture sleeve 25 that is disposed around the sheath assembly 20 to secure and protect the lead assembly 10 proximal to the site of transvenous entry.

In the initial phase of the implantation procedure for the lead assembly 10, an incision is made in the upper thoracic region above the areola, and a stylet 26 is introduced into the lead assembly 10. By manipulating the stylet 26, the lead tip 24 is introduced into one of the major veins leading to the heart, such as the subclavian vein or one of the internal jugular veins. The suture sleeve 25 is then sutured in place to secure the proximal end 14 of the lead assembly 10 proximal to the site of transvenous entry. After the lead tip 24 is initially introduced into one of the major veins, the lead assembly 10 is advanced by manipulation of the stylet 26 until the lead tip 24 passes through the superior vena cava 27 and into the desired location in the heart 12. For the purposes of this illustration, the particular endocardial location is the right ventricle 28.

Figure 4:
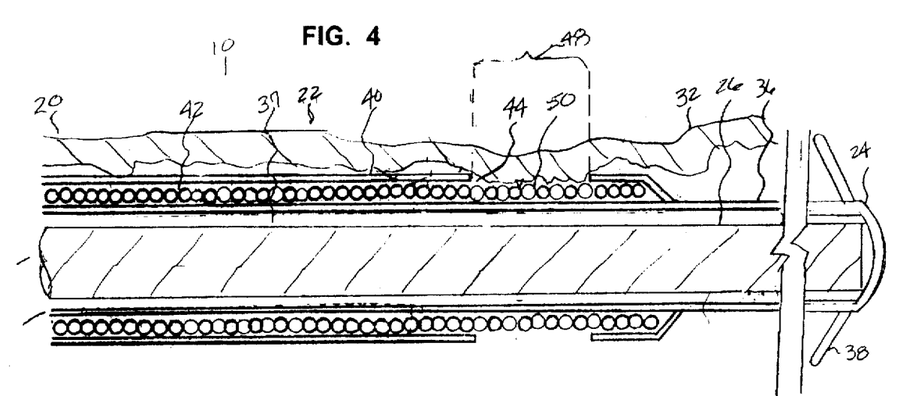
FIG. 4 is a sectional view of the distal end of the lead assembly of FIG. 1 prior to active lateral fixation.

Referring now to FIGS. 3 and 4, the detailed structure of the distal end 22 of the lead assembly 10 may be understood. FIG. 3 shows the lead assembly 10 advanced into the right ventricle 28 of the heart 12 such that the tip 24 is located in the ventricular apex 30 and a portion of the distal end 22 is disposed adjacent to a particular spot on the interventricular septum 32. The distal end 22 is brought into contact with the interventricular septum 32 by appropriate pre-bending and manipulation of the stylet 26. FIG. 4 shows a sectional view of the distal end 22. Note that the length of the distal end 22 requires the view in FIG. 4 to be broken. The tip 24 is a cup-like member that may be actively fixed to the heart 12 using a corkscrew, or passively via one or more tines 38 projecting therefrom as shown. If the tip 24 is configured to function as an electrode, the tip 24 may be fabricated from a metallic material, such as platinum-iridium alloy, titanium, stainless steel, or some other biocompatible conducting metal. The tip 24 need not be composed of a metallic material if a conducting path therethrough is unnecessary. In such circumstances, the tip 24 may be fabricated from a rigid biocompatible plastic material.

The sheath assembly 20 includes a first, or inner, sheath 36 that may be coupled at its proximal end to the connector 16 and at its distal end to the tip 24. The inner sheath 36 is generally tubular and includes a coextensive lumen 37 for receipt of the stylet 26. The inner sheath 36 is designed to stretch elastically to facilitate lateral fixation to the heart 12 as described more fully below. Accordingly, the inner sheath 36 is preferably composed of an elastic, electrically insulating, biocompatible material of the type commonly used to fabricate cardiac leads, such as silicone rubber. The sheath 36 need not extend proximally to the connector 16 or distally to the tip 24.

A second, or outer, sheath 40 is disposed around and coupled to the inner sheath 36, thereby defining an elongated annular space 42. The outer sheath 40 is generally tubular and is coupled to the connector 16 proximally, and may or may not be coterminous at its distal end with the inner sheath 36. In the embodiment shown in FIG. 4, the outer sheath 40 is not coterminous at its distal end with the inner sheath 36. An aperture 44 is provided in the outer sheath 40 that may extend around the entire circumference of the sheath 40 or only a portion thereof. The aperture 44 defines a gripping region 48 shown by the vertical dashed lines. The outer sheath 40 may be fabricated from the same elastic, electrically insulating, biocompatible material as the inner sheath 36. As noted above, the sheath 36 may be shorter than the sheath 40. In such an arrangement, the seam between the ends of the sheath 36 and the interior surface of the sheath 40 should be smoothly molded to avoid interfering with the stylet 26 during insertion.

A biasing wire 50 is disposed in the annular space 42. The biasing wire 50 may be coupled to the connector 16 proximally and is approximately coterminous at its distal end with the outer sheath 40. The biasing wire 50 has a plurality of coils exposed by the aperture 44 in the gripping region 48, and may be coiled along its entire length as shown. Although the biasing wire 50 will typically have a round cross-section, other geometries are possible, such as rectangular.

As discussed more below, the main function of the biasing wire 50 is to provide a mechanism to actively laterally fix the gripping region 48 to a particular spot in the heart 12. In this regard, the biasing wire has coil spring characteristics in the gripping region 48. Further biasing action is provided by the elasticity of the sheath 36, which may be fabricated to have a locally higher elasticity in the gripping region 48 than in the remainder of the sheath 36. However, depending upon the particular usage of the lead assembly 10, the biasing wire 50 may be coupled to the connector 16 and serve as a sensing electrode to receive electrical signals from the septum 32, or as a pacing/defibrillation electrode. Typical materials for the biasing wire 50 include titanium, platinum, stainless or similar materials.

Figures 5, 8, 9, 10, 11:
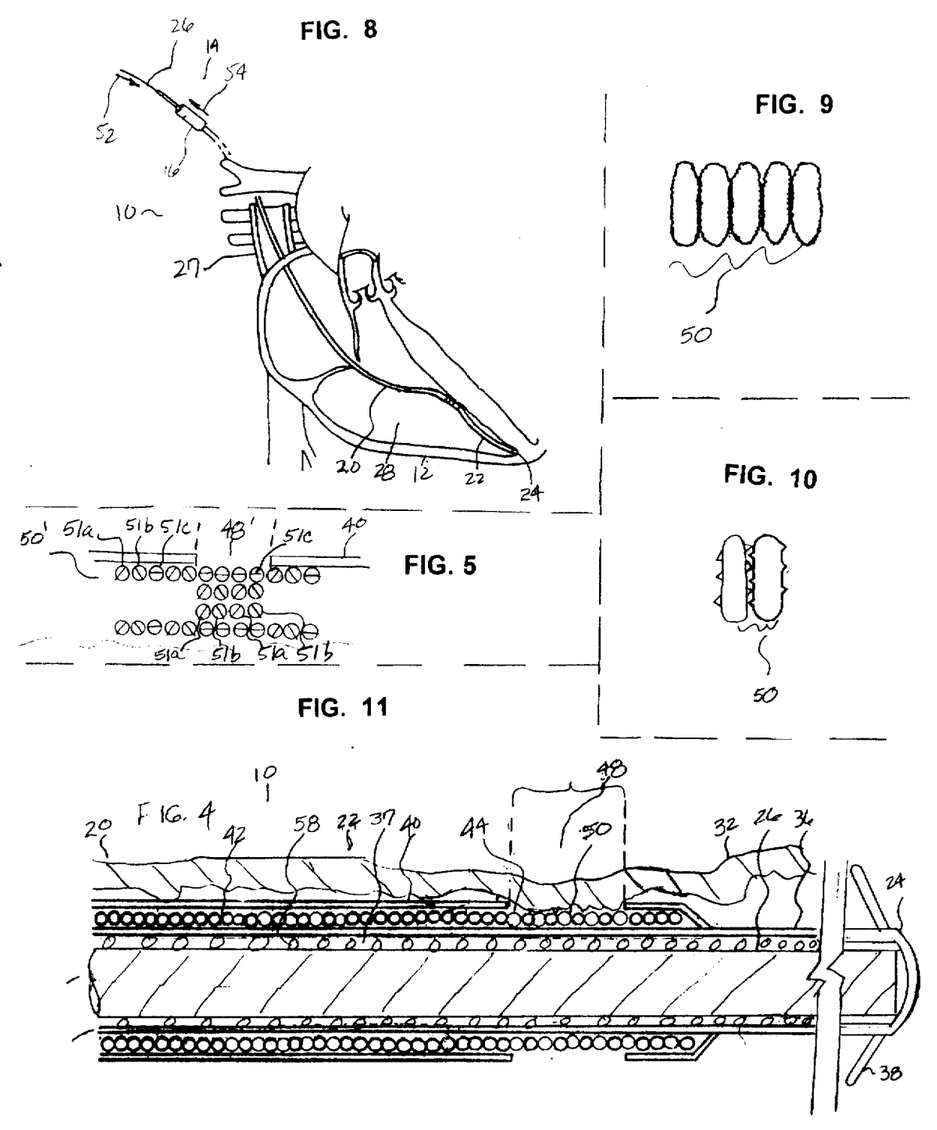
FIG. 5 is a sectional view of a portion of an alternate embodiment of the lead assembly in accordance with the present invention.
FIG. 8 is a sectional view of the distal end of the lead assembly of FIG. 1 during the active lateral fixation procedure.
FIG. 9 is a top view of an alternate embodiment of the biasing wire in the lead assembly that incorporates serrated coils.
FIG. 10 is a top view of another alternate embodiment of the biasing wire in the lead assembly that incorporates another type of serrated coil.
FIG. 11 is a sectional view of an alternate embodiment of the lead assembly in accordance with the present invention.

The biasing wire 50 may take on a variety of different configurations, such as the co-axial form shown in FIG. 4, or a variety of other arrangements, such as a trifilar, or a coated wire, such as a Thinline™ (trademark of Sulzer Intermedics, Inc.) where multiple coils are individually insulated, except in the gripping region 48. For example, FIG. 5 shows a sectional view of a portion of an alternate embodiment incorporating a Thinline™ arrangement for a biasing wire 50'. The view shows only the wire 50' and the sheath 40. The wire 50' includes three individually insulated coils 51a, 51b, and 51c. In the gripping region 48', the coils 51a and 51b are nested inside the coil 51c. In order for the coil 51c to function as an electrode, the insulation is removed from the portion of the coil 51c exposed in the gripping region 48'.

As noted above, the biasing wire 50 may take on a variety of configurations. However, it is anticipated that either the biasing wire 50 or the sheath 40, or both, should be configured so that the biasing wire 50 has at least two coils exposed by the aperture 44 in the gripping region 48 to provide a pincer action for grasping the heart 12.

Figure 6:
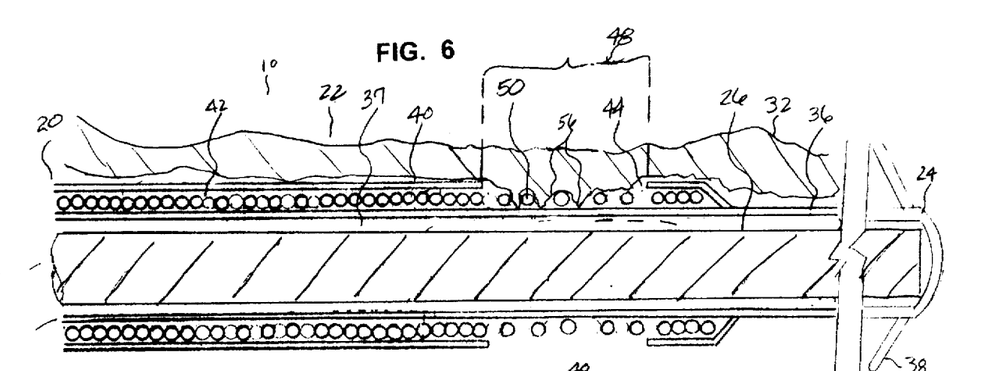
FIG. 6 is a sectional view of the distal end of the lead assembly of FIG. 1 during the active lateral fixation procedure.
Figure 7:
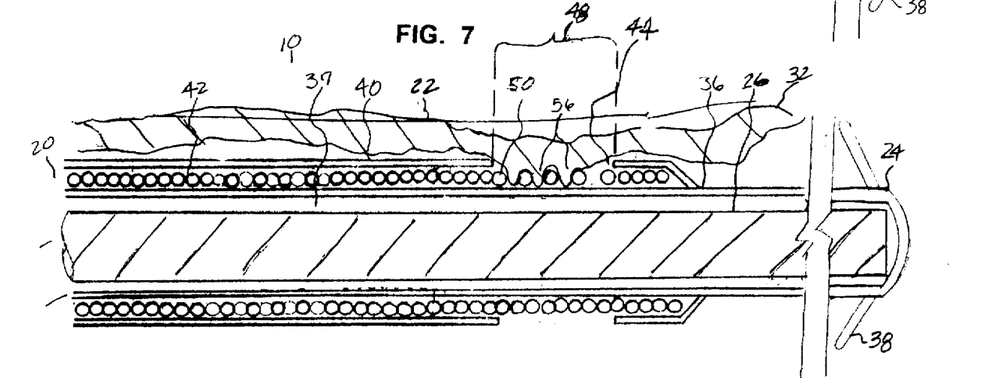
FIG. 7 is a sectional view of the distal end of the lead assembly of FIG. 1 at the conclusion of the active lateral fixation procedure.

The active lateral fixation of the distal end 22 to myocardial tissue may be understood by reference to FIGS. 4, 6, 7, and 8. After the distal end 22, and particularly the gripping region 48, are positioned proximate the interventricular septum 32 as shown in FIG. 4, an axial force is imparted on the stylet 26 in the direction indicated by the arrow 52 shown in FIG. 8. Simultaneously, force is applied in the opposite direction on the connector 16 as indicated by the arrow 54. As the stylet 26 bears against the tip 24, and force is applied to the connector 16, the sheath 36 and the biasing wire 50 stretch longitudinally to the expanded position shown in FIG. 6, thereby creating gaps between the individual coils of the biasing wire 50. For simplicity of illustration, the gaps in the coils of the biasing wire 50 are shown most prominently in the gripping region 48. The gaps between the individual coils of the biasing wire 50 provide interstices for eminences 56 projecting from the interventricular septum 32. The skilled artisan will appreciate that the interior surface of the right ventricle 28 is marked by substantial irregularities and projections or eminences, due to the presence of trabeculae carneae. After the lead assembly 10 has been stretched, load is removed from both the stylet 26 and the connector 16. The elasticity of both the inner sheath 36 and the biasing wire 50 urge the distal end 22 to contract to its original retracted position as shown in FIG. 7, thereby actively engaging the myocardial eminences 56 between the coils of the biasing wire 50 in the gripping region 48. The distal end 22 is now actively laterally fixed to the interventricular septum 32 in the vicinity of the gripping region 48. If the initial attempt to grasp the interventricular septum 32 is unsuccessful, the foregoing procedure may be repeated as often as necessary to achieve the desired fixation. Indeed, detachment of the gripping region 48 merely requires application of the forces shown in FIG. 8 along with an appropriate manipulation of the stylet 26 to move the distal end 22 away from the septum 32.

After the distal end 22 of the lead assembly 10 has been laterally fixed, tissue in-growth should proceed rapidly, providing a more robust attachment to the interventricular septum 32. To facilitate tissue in-growth, the biasing wire 50 may be coated with a porous biocompatible material, such as iridium oxide. To facilitate both tissue in-growth and the ability of the biasing wire 50 to engage the myocardium, the exterior surface of the biasing wire 50 may be provided with outwardly projecting serrations or opposable barbs as shown, respectively, in FIGS. 9 and 10. The serrations or barbs may be provided by knurling or other machining processes. These serrations or barbs not only provide a more tacky surface for the biasing wire 50, but also provide a plurality of interstices for tissue in-growth.

Several features may be incorporated into the lead assembly 10 to facilitate implantation and fixation. A biocompatible tissue adhesive may be applied to the sheath 40 or the biasing wire 50 in the vicinity of the gripping region 48 to assist in retaining the gripping region 48 in position. In addition, the gripping region 48 may be coated with a biocompatible dissolving material, such as polyethylene glycol or sucrose to facilitate smooth passage through the veins and the heart chambers and valves.

The embodiment disclosed in FIGS. 4, 6 and 7, includes a single biasing wire 50 that functions as an electrode, but is not coupled to the tip 24. However, a variety of other arrangements are possible. For example, as shown in FIG. 11, the lead assembly 10 may include a biasing wire 50 as disclosed above, as well as a conductor wire 58 that is disposed in the lumen 37 and coupled to the tip 24. In this configuration, sensing or stimulation may be carried out at both the tip 24 and the gripping region 48.

Figure 12:
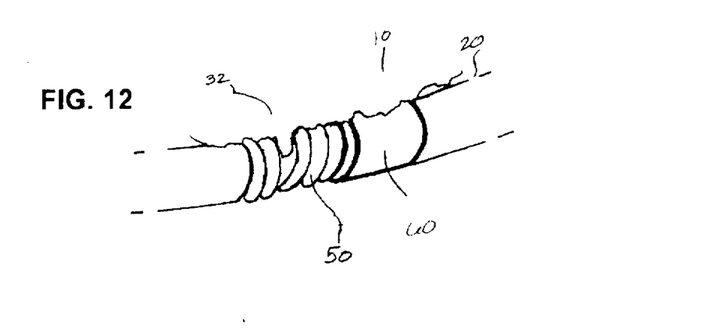
FIG. 12 is a pictorial view of an alternate embodiment of the lead assembly in accordance with the present invention; that incorporates an annular electrode.

In another variation of the present invention shown in FIG. 12, the distal end 22 of the lead assembly 10 may be fitted with an annular electrode 60 that may be coupled to the biasing wire 50, or an internal conductor wire (not shown) and may be disposed either proximally or distally to the exposed coils of the biasing wire 50.

Figure 13:
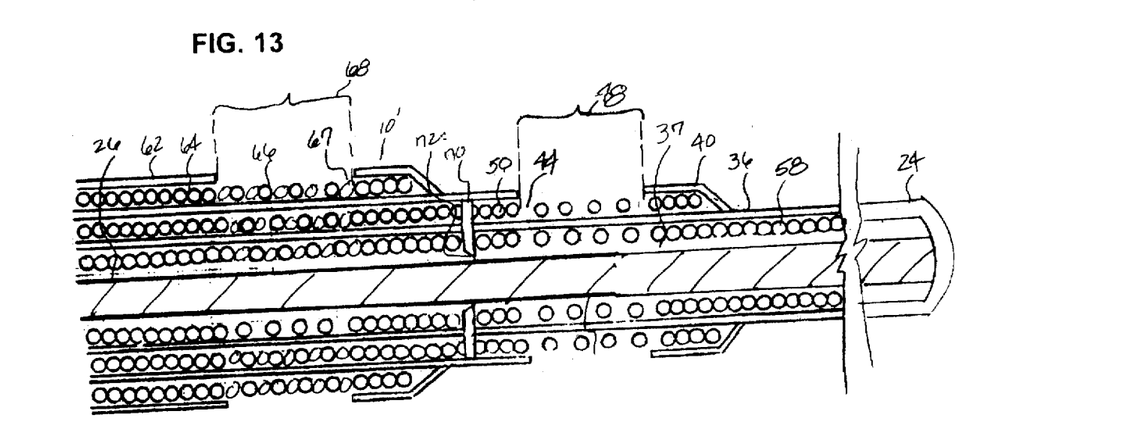
FIG. 13 is a sectional view of the distal end of a multiple fixation point embodiment of the lead assembly in accordance with the present invention.
Figure 14:
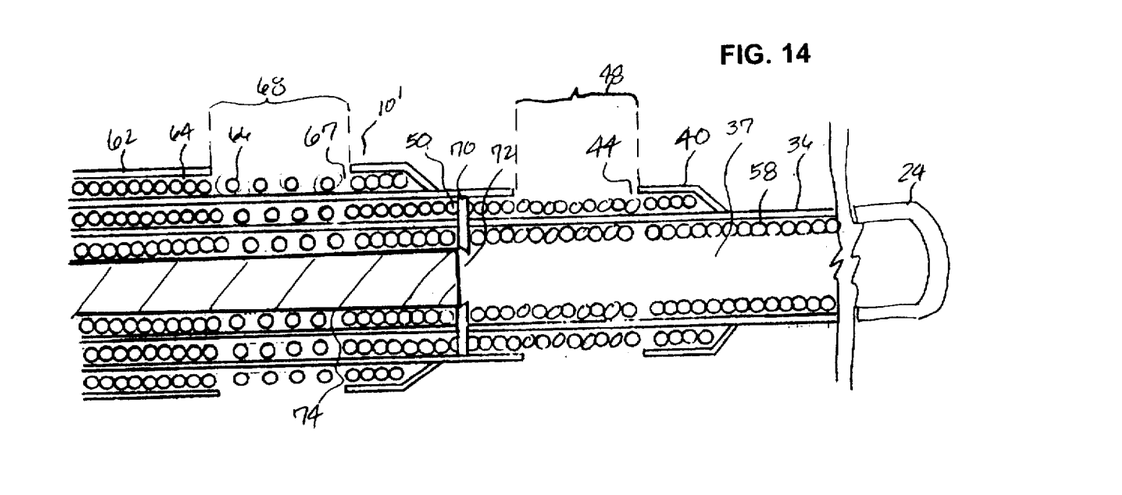
FIG. 14 is another sectional view of the distal end of a multiple fixation point embodiment of the lead assembly in accordance with the present invention.

FIGS. 13 and 14 disclose an alternate embodiment of the lead assembly 10' that is capable of simultaneous active lateral fixation at more than one point. The embodiment of the lead assembly 10' contains many of the elements from the embodiments disclosed above, namely, the inner sheath 36, the outer sheath 40 with the aperture 44, the biasing wire 50, the tip 24, and the internal conductor wire 58 that is coupled to the tip 24. In addition, the lead assembly 10' is fitted with a second outer sheath 62 that is disposed around the first outer sheath 40 and is coterminous proximally with the inner sheath 40, and terminates distally at a point that is proximal from the gripping region 48. The second outer sheath 62 and the first outer sheath 40 define an annular space 64 in which a second and additional biasing wire 66 is disposed. Like the first outer sheath 40, the second outer sheath 62 includes an aperture 67 to provide a second gripping region 68 indicated by the vertical dashed lines.

Active lateral fixation of the lead assembly 10' at the gripping region 48 may be accomplished as described above with regard to FIGS. 4, and 6–8. However, the skilled artisan will appreciate that after the lead assembly 10' is laterally fixed at the gripping region 48, any attempt to fix the lead assembly 10' at the gripping region 68 by imparting an axial force on the tip 24 via the stylet 26 will simply stretch the entire lead assembly 10' and potentially dislodge the previously attached gripping region 48. To alleviate this potential difficulty in laterally attaching the lead assembly 10' at a second location, an annular blocking member 70 is provided. The annular blocking member 70 has a central opening 72 that is disposed within the lumen 37, and has a diameter sized to permit the stylet 26 to pass therethrough. The opening 72 is countersunk at the proximal side of the blocking member 70 to facilitate easy passage of the stylet 26. The peripheral surface of the annular blocking member 70 is coupled to the first outer sheath 40.

To laterally fix the lead assembly 10' at the gripping region 48, the stylet 26 is introduced past the annular blocking member 70 and manipulated as disclosed above. After the gripping region 48 has been laterally fixed, the gripping region 68 may then be laterally fixed by withdrawing the stylet 26 and inserting a second stylet 74, which has a diameter that is slightly larger than the diameter of the opening 72. In this regard, the annular blocking member 70 provides a thrust surface against which the larger diameter stylet 74 may bear to stretch the lead assembly 10' in the vicinity of the gripping region 68, without dislodging the gripping region 48. As with the gripping region 48, when pressure is removed from the stylet 74, the coils of the biasing wire 66 in the gripping region 68 engage the myocardium to laterally fix the lead assembly 10' at a second location. If the initial attempt to grasp the myocardium is unsuccessful, the foregoing procedure may be repeated as often as necessary to achieve the desired fixation.

Figure 15:
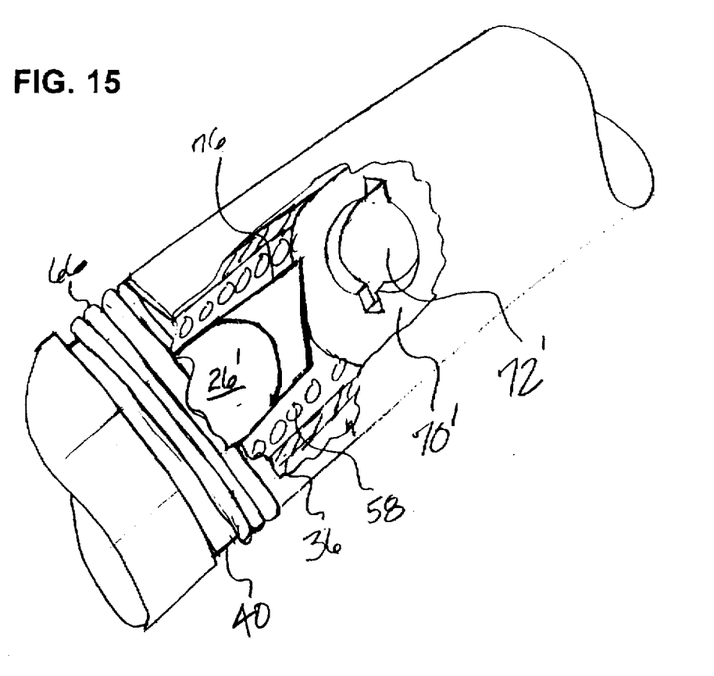
FIG. 15 is a pictorial view of a portion of an alternative lead assembly and stylet.

In an alternate embodiment of the assembly shown in FIGS. 13 and 14, structure may be included that facilitates the spreading of adjacent coils of the biasing wire 66. FIG. 15 shows such an alternative embodiment where an annular member 70' is provided with a slotted opening 72'. A stylet 26' is fashioned with a flattened tip 76 that is keyed to the slotted opening 72'. By inserting the tip 76 into the slotted opening 72' and rotating the stylet 26' in the appropriate direction relative to the winding of the wire 66, the coils of the wire 66 may be spread apart. Reverse rotation of the stylet 26' removes the bias, enabling the wire 66 to return to a neutral position.

The skilled artisan will appreciate that the number, spacing, and size of the various gripping regions 48 and 68 depicted above, as well as their order of attachment to myocardial tissue may be varied to suit the particular medical requirements for a given patient. Furthermore, it should be apparent that the foregoing description of fixation to the interventricular septum is merely illustrative. Other possible applications include, among others, tip placement in the ventricular apex with lateral fixation on the right atrial free wall, tip placement in the ventricular apex with lateral fixation on the interventricular septum extending up to the outflow tract, tip placement in the right atrial appendix with lateral fixation in the coronary sinus ostium, or tip placement in the outflow tract with lateral fixation on the upper interventricular septum.

While the invention may be susceptible to various modifications and alternative forms, specific embodiments shown by way of example in the drawings have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead assembly having an expanded position and a retracted position, comprising:
    a connector for attachment to a cardiac stimulator; and
    a sheath assembly coupled to said connector, said sheath assembly comprising
    a first elastic insulating sheath having a lumen defined thereby;
    a first biasing wire disposed around said first sheath and coupled to said connector to provide an electrical pathway therefrom, said biasing wire having a first plurality of coils and a distal end; and
    a second elastic insulating sheath disposed over and coupled to said first sheath and having an aperture exposing at least two of said first plurality of coils, said at least two of said first plurality of coils being operable to engage a portion of myocardial tissue between said at least two of said first plurality of coils when said lead assembly is moved from said expanded position to said retracted position.

2. The cardiac lead assembly of claim 1, comprising a first electrode coupled to said distal end of said biasing wire.

3. The cardiac lead assembly of claim 1, comprising a conducting wire coupled to said connector and a second electrode coupled to said conducting wire.

4. The cardiac lead assembly of claim 1, wherein each of said at least two coils has a plurality of barbs to facilitate engagement of said portion of myocardial tissue.

5. The cardiac lead assembly of claim 1, wherein each of said at least two coils has a plurality of serrations to facilitate engagement of said portion of myocardial tissue.

6. The cardiac lead assembly of claim 1, comprising:
    a second biasing wire disposed around said second sheath, said second biasing wire having a second plurality of coils;
    an annular member coupled to said second sheath, said annular member having a central opening disposed in said lumen and having a first diameter; and
    a third elastic insulating sheath disposed over and coupled to said second sheath and having a second proximal portion and a second distal portion, said second proximal portion and said second distal portion being separated a preselected distance to expose at least two of said second plurality of coils, said at least two of said second plurality of coils being operable to engage a portion of myocardial tissue between said at least two of said second plurality of coils when a stylet having a diameter larger than said first diameter is inserted into said lumen and engages said annular member and said lead assembly is moved from said expanded position to said retracted position.

7. A cardiac lead assembly having an expanded position and a retracted position, comprising:
    a connector for attachment to a cardiac stimulator; and
    a sheath assembly coupled to said connector, said sheath assembly comprising:
    a first elastic insulating sheath having a lumen defined thereby;
    a first biasing wire disposed around said first sheath, said biasing wire having a first plurality of coils and a distal end;
    a second elastic insulating sheath disposed over and coupled to said first sheath and having a first aperture exposing at least two of said first plurality of coils, said at least two of said plurality of coils being operable to engage a portion of myocardial tissue between said at least two of said plurality of coils when said lead assembly is moved from said expanded position to said retracted position;
    a second biasing wire disposed around said second sheath, said second biasing wire having a second plurality of coils, said first and second biasing wires being coupled to said connector to provide electrical pathways therefrom;

an annular member coupled to said second sheath, said annular member having a central opening disposed in said lumen and having a first diameter; and a third elastic insulating sheath disposed over and coupled to said second sheath and having a second aperture exposing at least two of said second plurality of coils, said at least two of said second plurality of coils being operable to engage a portion of myocardial tissue between said at least two of said second plurality of coils when a stylet having a diameter larger than said first diameter is inserted into said lumen and engages said annular member and said lead assembly is moved from said expanded position to said retracted position.

8. The cardiac lead assembly of claim 7, comprising a first electrode coupled to said distal end of said first biasing wire.

9. The cardiac lead assembly of claim 7, comprising a conducting wire coupled to said connector and a second electrode coupled to said conducting wire.

10. The cardiac lead assembly of claim 7, wherein each of said at least two of said first and said second plurality of coils has a plurality of barbs to facilitate engagement of said portion of myocardial tissue.

11. The cardiac lead assembly of claim 7, wherein each of said at least two of said first and said second plurality of coils has a plurality of serrations to facilitate engagement of said portion of myocardial tissue.

12. A cardiac stimulation system, comprising:

a cardiac stimulator; and a cardiac lead assembly coupled to said cardiac stimulator, said cardiac lead assembly comprising:

a connector attached to said stimulator;

a first elastic insulating sheath coupled to said connector;

a biasing wire disposed around said first sheath and coupled to said connector to provide an electrical pathway therefrom, said biasing wire having a plurality of coils and a distal end; and a second elastic insulating sheath disposed over said first sheath and having a first aperture exposing at least two of said coils, said at least two coils being operable to engage a portion of myocardial tissue between said at least two coils when said lead assembly is moved from an expanded position to a retracted position.

13. The cardiac lead assembly of claim 12, comprising a first electrode coupled to said distal end of said biasing wire.

14. The cardiac lead assembly of claim 12, comprising a conducting wire coupled to said connector and a second electrode coupled to said conducting wire.

15. The cardiac lead assembly of claim 12, wherein each of said at least two coils has a plurality of barbs to facilitate engagement of said portion of myocardial tissue.

16. The cardiac lead assembly of claim 12, wherein each of said at least two coils has a plurality of serrations to facilitate engagement of said portion of myocardial tissue.

17. The cardiac stimulation system of claim 12, comprising:

a second biasing wire disposed around said second sheath, said second biasing wire having a second plurality of coils and being coupled to said connector to provide an electrical pathway therefrom;

an annular member coupled to said second sheath, said annular member having a central opening disposed in said lumen and having a first diameter; and a third elastic insulating sheath disposed over and coupled to said second sheath and having a second aperture exposing at least two of said second plurality of coils, said at least two of said second plurality of coils being operable to engage a portion of myocardial tissue between said at least two of said second plurality of coils when a stylet having a diameter larger than said first diameter is inserted into said lumen and engages said annular member and said lead assembly is moved from said expanded position to said retracted position.

\* \* \* \* \*